US012667325B2

(12) United States Patent
Lee et al.

(10) Patent No.: US 12,667,325 B2
(45) Date of Patent: Jun. 30, 2026

(54) INSPIRATION SYSTEM RELATED SYMPTOM SENSING SYSTEM, APPARATUS, AND METHOD

(71) Applicant: ASG Inspiration Laboratory Ltd., Kowloon (HK)

(72) Inventors: Johnson Lee, Kowloon (HK); Jao Juen Hung, Kowloon (HK); Sung Tsai Yu, Kowloon (HK); Shih Pan Chao, Kowloon (HK); Hao-Wei Huang, Kowloon (HK); Wen-Hui Fu, Kowloon (HK); Hsin-Ke Li, Kowloon (HK)

(73) Assignee: ASG Inspiration Laboratory Ltd., Kowloon (HK)

( * ) Notice: Subject to any disclaimer, the term of this patent is extended or adjusted under 35 U.S.C. 154(b) by 319 days.

(21) Appl. No.: 18/398,393

(22) Filed: Dec. 28, 2023

(65) Prior Publication Data

US 2025/0000477 A1 Jan. 2, 2025

(30) Foreign Application Priority Data

Jun. 30, 2023 (TW) .................................. 112124536

(51) Int. Cl.
*A61B 7/00* (2006.01)
*A61B 5/00* (2006.01)

(52) U.S. Cl.
CPC ............ *A61B 7/003* (2013.01); *A61B 5/4845* (2013.01); *A61B 5/7203* (2013.01); *A61B 5/7267* (2013.01); *A61B 5/7282* (2013.01)

(58) Field of Classification Search
None
See application file for complete search history.

(56) References Cited

U.S. PATENT DOCUMENTS

2019/0388056 A1 12/2019 Rodriquez

FOREIGN PATENT DOCUMENTS

CN 107374632 A 11/2017
CN 108814642 B 7/2021
(Continued)

OTHER PUBLICATIONS

Lo Presti et al. ; A Soft and Skin-Interfaced Smart Patch Based on Fiber Optics for Cardiorespiratory Monitoring; Biosensors (Basel) . May 26, 2022;12(6):363. doi: 10.3390/bios12060363 (Year: 2022).*

(Continued)

*Primary Examiner* — Jay B Shah
(74) *Attorney, Agent, or Firm* — CKC & Partners Co., LLC

(57) ABSTRACT

An inspiration system related symptom sensing system includes a patch and a processor. The patch includes at least one vibrator and a plurality of receivers. Each of the receivers is configured to generate a reference vibration signal corresponding to the vibrator and a vibration signal corresponding to an inspiration system of an organism. The processor is configured to determine a relative position of each of the receivers related to the inspiration system of the organism based on the reference vibration signals, the vibration signals, and a plurality of positional relationships of the vibrator corresponding to each of the receivers. The processor is configured to generate a spatial position corresponding to the inspiration system and a corresponding symptom type by using a classification model based on the abnormal signals and the relative positions corresponding to the receivers.

20 Claims, 3 Drawing Sheets

(56)                References Cited

FOREIGN PATENT DOCUMENTS

| CN | 113436726 | B | 3/2022 |
|----|-----------|---|--------|
| TW | I651076 | B | 2/2019 |
| TW | I669100 | B | 8/2019 |
| TW | I687206 | B | 3/2020 |
| TW | M594440 | U | 5/2020 |
| TW | I761719 | B | 4/2022 |
| TW | I769449 | B | 7/2022 |
| TW | I771077 | B | 7/2022 |
| TW | M647887 | U | 11/2023 |

OTHER PUBLICATIONS

Mu Junjie et al., "Design of voiceprint recognition system based on CNN-LSTM neural network", Application of Electronic Technique, 2021, 47(3):75-78.
Luca Brunese et al., "Deep learning for heart disease detection through cardiac sounds", Procedia Computer Science vol. 176, 2020, pp. 2202-2211.
Jonathan Rubin et al., "Recognizing Abnormal Heart Sounds Using Deep Learning", IJCAI 2017 Knowledge Discovery in Healthcare Workshop.
Chia-Hsien Lin, "Implementation of Lung Sound Acquisition and Analysis System", A thesis submitted for degree of Master of Science Institute of Biomedical Engineering, National Cheng Kung University, 2007.
Hsiao-Huang Chang, "Biomedical Signal Analysis Using Holo-Hilbert Spectral Analysis", A thesis submitted for degree of Doctor of Department of Electrical Engineering, National Central University, 2019.

* cited by examiner

INSPIRATION SYSTEM RELATED SYMPTOM SENSING SYSTEM, APPARATUS, AND METHOD

CROSS-REFERENCE TO RELATED APPLICATION

This application claims priority to Taiwan Application Serial Number 112124536, filed Jun. 30, 2023, which is herein incorporated by reference in its entirety.

BACKGROUND

Field of Invention

The present disclosure relates to a symptom sensing system, apparatus, and method. More particularly, the present disclosure relates to an inspiration system related symptom sensing system, apparatus, and method.

Description of Related Art

The current clinical method of diagnosing a patient's inspiration system is for a physician to listen to the patient's lung sounds with a stethoscope, and further determine the type and position of the symptoms based on the lung sounds. However, the range of sounds or vibrations that the human ear can hear is limited in amplitude and frequency. Sounds with frequencies that are too high or too low and subtle sounds cannot be heard. In addition, doctors are not able to continuously monitor the patient's lung sounds and the patient's lung symptoms for a long time.

On the other hand, when animal experiments are currently carried out in drug experiments, in order to confirm changes in drug concentration in the animal's blood after taking the drug, it is necessary to draw blood from the animals at different stages. However, animals (e.g. mice) have limited blood, which limits the number of blood draws. In addition, obtaining pathological sections is needed to observe the changes in symptom in animals, and it is impossible to continuously monitor the symptoms in a non-invasive way.

In view of this, how to improve the accuracy of detecting lung sounds and perform long-term monitoring to diagnose the patient's symptom type, position, severity, etc., is a possible and feasible goal.

SUMMARY

The disclosure provides an inspiration system related symptom sensing system comprising a patch and a processor. The patch is configured to detect a vibration generated by an inspiration system corresponding to an organism and comprises at least one vibrator and a plurality of receivers. The at least one vibrator is configured to generate a reference vibration. The processor is communicatively connected to the patch. Each of the receivers is configured to detect the reference vibration corresponding to the at least one vibrator to generate a reference vibration signal respectively. Each of the receivers is configured to detect the vibration generated by the inspiration system corresponding to the organism to generate a vibration signal respectively. The processor is configured to determine a relative position of each of the receivers related to the inspiration system of the organism based on the reference vibration signals, the vibration signals, and a plurality of positional relationships of the at least one vibrator corresponding to each of the receivers. The processor is configured to extract an abnormal signal from each of the vibration signals. The processor is configured to generate a spatial position corresponding to the inspiration system of the organism and a symptom type corresponding to the spatial position by using a classification model based on the abnormal signals of the vibration signals and the relative positions corresponding to the receivers.

The disclosure further provides an inspiration system related symptom sensing apparatus comprising a transceiver interface and a processor. The transceiver interface is communicatively connected to a patch, wherein the patch comprises at least one vibrator and a plurality of receivers. The processor is electrically connected to the transceiver interface. The transceiver interface is configured to receive a plurality of reference vibration signals corresponding to the at least one vibrator and a plurality of vibration signals corresponding to an inspiration system corresponding to an organism from the patch. The processor is configured to determine a relative position of each of the receivers related to the inspiration system of the organism based on the reference vibration signals, the vibration signals, and a plurality of positional relationships of the at least one vibrator of the patch corresponding to each of the receivers of the patch. The processor is configured to extract an abnormal signal from each of the vibration signals. The processor is configured to generate a spatial position corresponding to the inspiration system of the organism and a symptom type corresponding to the spatial position by using a classification model based on the abnormal signals of the vibration signals and the relative positions corresponding to the receivers.

The disclosure further provides an inspiration system related symptom sensing method. The inspiration system related symptom sensing method is adapted for use in an inspiration system related symptom sensing system, wherein the inspiration system related symptom sensing system comprises a processor and a patch, the patch comprises at least one vibrator and a plurality of receivers. Each of the receivers is configured to detect a reference vibration corresponding to the at least one vibrator to generate a reference vibration signal respectively. Each of the receivers is configured to detect the vibration generated by the inspiration system corresponding to an organism to generate a vibration signal respectively. The processor is configured to determine a relative position of each of the receivers related to the inspiration system of the organism based on the reference vibration signals, the vibration signals, and a plurality of positional relationships of the at least one vibrator corresponding to each of the receivers. The processor is configured to extract an abnormal signal from each of the vibration signals. The processor is configured to generate a spatial position corresponding to the inspiration system of the organism and a symptom type corresponding to the spatial position by using a classification model based on the abnormal signals of the vibration signals and the relative positions corresponding to the receivers.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
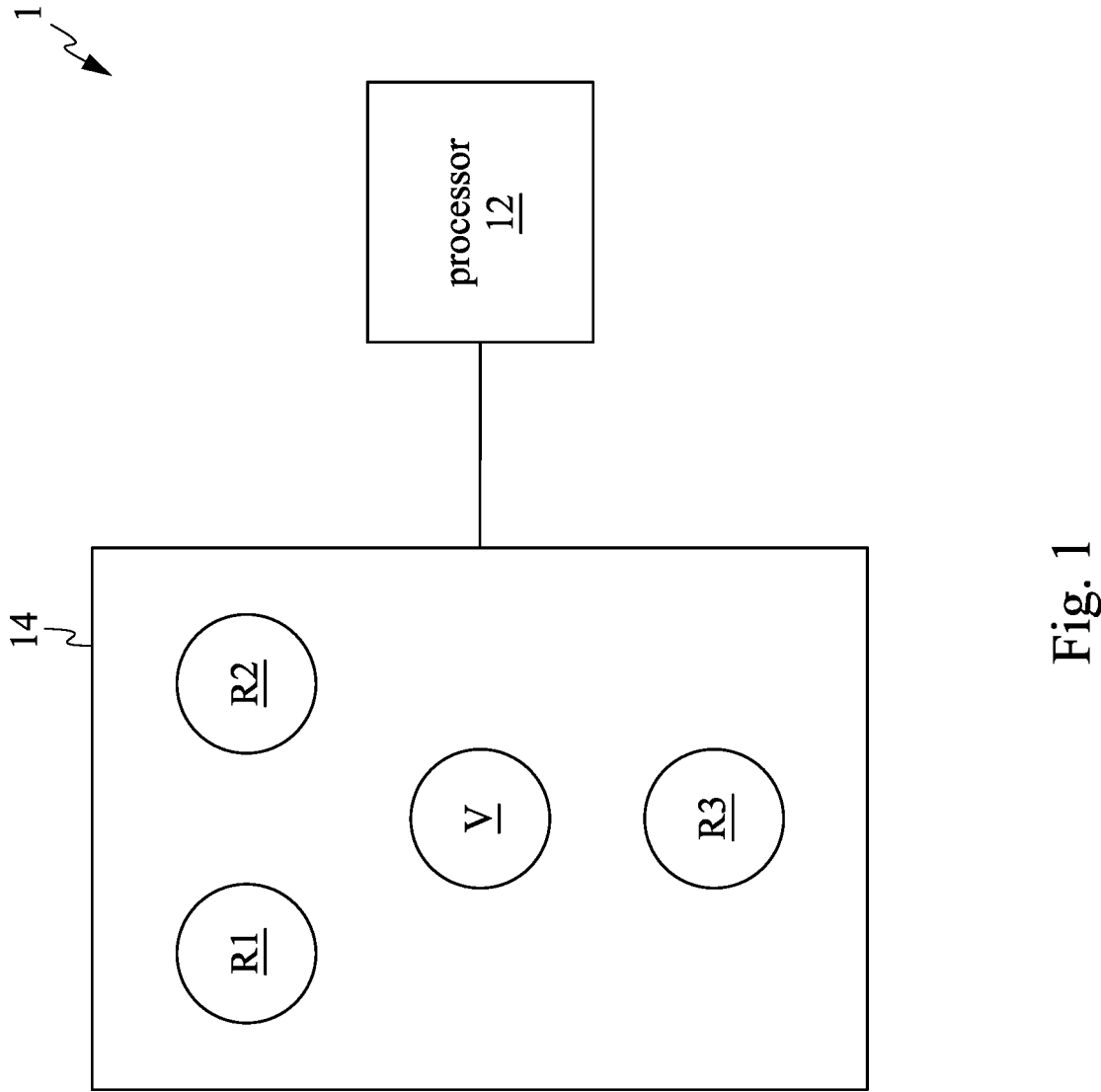
FIG. 1 is a schematic diagram illustrating an inspiration system related symptom sensing system according to a first embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1. FIG. 1 is a schematic diagram illustrating an inspiration system related symptom sensing system 1 according to a first embodiment of the present disclosure. The inspiration system related symptom sensing system 1 comprises a processor 12 and a patch 14, wherein the processor 12 is communicatively connected to the patch 14. The inspiration system related symptom sensing system 1 is configured to determine the physiological state in an organism based on vibrations or sounds of the organism.

In some embodiments, the processor 12 can comprise a central processing unit (CPU), a multi-processor, a distributed processing system, an application specific integrated circuit (ASIC), and/or a suitable processing unit.

The patch 14 comprises a vibrator V and receivers R1, R2, and R3. The patch 14 is configured to stick on the surface of an organism and detect vibrations (can also be understood as sounds) generated by organs in the inspiration system of the organism (e.g., bronchi, lungs, trachea) by the receivers R1, R2, and R3. The vibrator V is configured to generate a reference vibration, and each of the receivers R1, R2, and R3 can determine relative positions relative to the organism based on the reference vibration and the vibrations generated by the organism (e.g., heart sounds, lung sounds).

It is noted that, a patch can comprises one or more vibrators, and there is no particular limitation in the present disclosure. It is understood that, the determination result can be more precise based on multiple vibrators. For clarity, the vibrator V will be taken as an example in the following embodiments.

In some embodiments, the patch 14 is a flexible film set configured with the vibrator V and the receivers R1, R2, and R3. Also, the vibrator V and the receivers R1, R2, and R3 of the patch 14 can exchange control signals and data via wire or wirelessly.

In some embodiments, the vibrator V is an electronic apparatus configured to generate vibrations and sounds, e.g., vibration unit, sound unit. The vibrator V is configured to provide a reference vibration source, and the reference vibration can be used for correcting the signal of the receivers. The reference vibration can also be taken as a basis for the receivers to calculate the relative positions with other vibration sources (e.g., heart, lungs). Besides, the reference vibration can be further taken as a basis for adjusting parameters corresponding to different organisms. Since the transmission efficiencies of vibrations in different kinds of body tissue are different, e.g., the transmission efficiency in fat is lower than in muscle, thus, the body tissue combinations of organisms can be estimated with known frequency and power of the reference vibrations.

In some embodiments, the receivers R1, R2, and R3 are electronic units configured to detect and transform vibrations and sounds into signals, e.g., microphone.

In some embodiments, the patch 14 can be placed on the surface of the organism closed to heart and lungs (e.g., human chest) to make the receivers R1, R2, and R3 able to detect clear heart sounds and lung sounds.

It is noticed that, since organisms are three-dimensional objects, the surface that the patch 14 placed on may not flat but curved or other shaped. Therefore, in order to locate the position of the receivers R1, R2, and R3 relative to organs of the organism in three-dimensional space, the inspiration system related symptom sensing system 1 needs to be configured with 3 or more receivers. However, the numbers of the vibrator V and the receivers R1, R2, and R3 in the present embodiment are only for ease of understanding. In other embodiments, the patch of the inspiration system related symptom sensing system can configured with more receivers and vibrators used for reference vibration sources.

Furthermore, the positional relationships between the vibrator V and the receivers R1, R2, and R3 set on the patch 14 are known. For example, in the embodiment shown in FIG. 1, the receiver R1 can be located 15 centimeters above and left of the vibrator V, the receiver R2 can be located 15 centimeters above and right of the vibrator V, and the receiver R3 can be located 15 centimeters below the vibrator V. However, the embodiment mentioned above can be understood as an example, in practical, the size of the patch 14 and the positional relationships between the vibrator V and the receivers R1, R2, and R3 can be adjusted based on context applied. For example, the size of the patch configured to detect humans can be roughly the area of a human chest, and the vibrator and the receivers can be evenly distributed in the patch to ensure that the vibrations from various areas of the lungs can be detected. On the other hand, the size of the patch configured to detect mice can be adjusted as the area corresponding to a mouse's lungs, and the distances and the distributions between the vibrator and the receivers can also be adjusted to ensure that the vibrations from various areas of the lungs can be detected.

After the patch 14 is placed on the surface of the organism, since the body shape and internal organs position of individual organisms are varied, the relative positions between the receivers R1, R2, and R3 and the heart, lungs, and/or other organ of the organism need to be confirmed first.

First, each of the receivers R1, R2, and R3 detects the reference vibration corresponding to the vibrator V to generate a reference vibration signal respectively.

After the vibrator V vibrates on the surface of the organism, each of the receivers R1, R2, and R3 can detect the reference vibration and generate the reference vibration signals respectively, wherein the reference vibration signals can comprise the frequency, amplitude, and detected time of the vibration.

Next, each of the receivers R1, R2, and R3 detects the vibration generated by the inspiration system corresponding to the organism to generate a vibration signal respectively.

The receivers R1, R2, and R3 detect the vibration of the organism, e.g., heart sounds and/or lung sounds, and generate the vibration signals respectively, the vibration signals can comprise the frequency, amplitude, and detected time of the vibration.

It is noticed that, the operations of the receivers R1, R2, and R3 detecting the vibration and the reference vibration are not limited to the sequence mentioned above and can be performed in other order or simultaneously. Also, the receivers R1, R2, and R3 can separate the vibration from the organism and the reference vibration from the vibrator V by using spectrum transformation or other methods.

Next, the processor 12 determines a relative position of each of the receivers R1, R2, and R3 related to the inspiration system of the organism based on the reference vibration signals, the vibration signals, and a plurality of positional relationships of the vibrator V corresponding to each of the receivers R1, R2, and R3.

After the processor 12 receives the corresponding reference vibration signals and vibration signals from the receivers R1, R2, and R3, since the relative position and distance between the vibrator V and each of the receivers R1, R2, and R3 are known, the processor 12 can calculate the relative position of each of the receivers R1, R2, and R3 relative to the vibration sources (e.g., heart, lungs) in the organism by using Time of Flight method and the triangulation method.

In some embodiments, the processor 12 can also establish a three-dimensional model based on the relative positions obtained, and the three-dimensional model comprises the patch 14 and the heart, lungs, and/or organs in the inspiration system of the organism configured to represent the positional relationships between the patch 14 and the organs in the three-dimensional space and the volume of each of the organs.

Specifically, when the heart and the organs in the inspiration system of the organism are functioning, each part of the organs (e.g., heart valves, bronchi, lungs) will vibrate regularly. Therefore, the inspiration system related symptom sensing system 1 can further obtain the sizes and relative positions of the heart and the organs in the inspiration system through calculating the positions of the organs based on vibrations from different parts.

Next, the processor 12 extracts an abnormal signal from each of the vibration signals.

Since the vibrations generated by each part of the heart and the organs in the inspiration system of the organism in good health are regular, the processor 12 can remove vibration signals of healthy heart and healthy organs in the inspiration system to obtain vibration signals of the heart and the organs in the inspiration system with abnormal symptoms (i.e., the abnormal signal).

In some embodiments, the processor 12 can transform the vibration signals into spectrum signals based on a frequency domain by using a spectrum transformation method (e.g., Fourier transform, wavelet transform, and Hilbert-Huang transform) and extracts the abnormal signal through remove the vibration signals of healthy heart and healthy organs in the inspiration system from the spectrum signals.

Finally, the processor 12 generates a spatial position corresponding to the inspiration system of the organism and a symptom type corresponding to the spatial position by using a classification model based on the abnormal signals of the vibration signals and the relative positions corresponding to the receivers R1, R2, and R3.

Specifically, after the processor 12 confirms the relative positions of the receivers R1, R2, and R3 related to the organism, the processor 12 determines the symptom type corresponding to the abnormal signals based on the abnormal signals and a trained machine learning model (i.e., the classification model) to determine symptoms inside the organism. For example, determining whether there is phlegm in a specific position in the lungs or the lungs are healthy (i.e., without symptoms) based on the vibration generated by the lungs, wherein the processor 12 can locate the position of the corresponding physiological state based on the frequency, amplitude, detected time, and/or other information of the abnormal signals.

In some embodiments, the processor 12 can also determine the severity of symptoms corresponding to the abnormal signals by using the classification model based on the abnormal signals, e.g., determining which stage of lung cancer the organism is in.

In some embodiments, the processor 12 can calculate the corresponding spatial position based on the abnormal signals by using Time of Flight method and the triangulation method to determine the symptom position.

It is noticed that, the spatial position described in the present disclosure is a position corresponding to the abnormal signals in the three-dimensional space configured by the inspiration system of the organism. However, the spatial position is not limited to a point and can also be an area composed of a two-dimensional plane or a space composed of a three-dimensional space. For example, if the inspiration system related symptom sensing system 1 determines that there is a symptom of pulmonary fibrosis in an area of the left lung based on the abnormal signals, and the spatial position is corresponding to the range of the area.

In some embodiments, the processor 12 generates a lung sound signal corresponding to the inspiration system of the organism based on each of the vibration signals; and the processor 12 generates the spatial position in the inspiration system of the organism and the symptom type corresponding to the spatial position based on the lung sound signals and the relative positions corresponding to the receivers.

In view of the vibrations corresponding to the organism detected by the receivers R1, R2, and R3 may be vibrations overlaid by heart sounds and lung sounds, the processor 12 can further split the vibration signals into lung sound signals, heart sound signals, and noise before determining the physiological state of the organism. Furthermore, the processor 12 generates a symptom diagnostic result corresponding to a specific position in the inspiration system of the organism based on the lung sound signals.

It is noticed that, the processor 12 can filter the noise and the heart sound signals from the vibration signals to extract the lung sound signals by using multiple technical means. For example, the processor 12 can split the heart sound signals and the lung sound signals by using a trained neural network (e.g., long short term memory network (LSTM)), or the processor 12 can also split the heart sound signals and the lung sound signals by using a wavelet threshold after filtering low-frequency noises by using a high-pass filter. The means of splitting the heart sound signals and the lung sound signals mentioned above are used for examples and the present disclosure is not limited thereto.

In some embodiments, the classification model is generated through training a machine learning model based on a plurality of history abnormal signals and a symptom diagnostic result corresponding to each of the history abnormal signals; and taking the trained machine learning model as the classification model.

The classification model can be a trained machine learning model trained by using a training set. For example, the inspiration system related symptom sensing system 1 obtains vibration signals from patients clinically and extracts corresponding abnormal signals (i.e., the history abnormal signals) through above-mentioned operations. After that, the physician confirms the type, location, range and severity of the patient's symptom (i.e., the symptom diagnostic result) after diagnosis through X-ray, auscultation, photography or other methods, and then the inspiration system related symptom sensing system 1 can train the machine learning model after obtaining the training data and the corresponding label to generate the classification model, wherein the classification model can calculate the symptom type corresponding to the vibration signals and a possibility of the organism having the symptom type.

In some embodiments, the processor 12 generates a concentration diagnostic result based on the vibration signals by using a concentration model, wherein the concentration diagnostic result is configured to represent a drug concentration trend in blood of the organism.

Apart from confirming whether there are symptoms in the organism, the inspiration system related symptom sensing system 1 is also configured to determine the drug concentration trend in blood of the organism after the organism takes drugs, wherein the concentration model can be built by the correspondence between the drug concentration trends in blood of the organism and the vibration signals obtained from multiple experiments.

In some embodiments, the concentration model is generated through training a machine learning model based on a plurality of history vibration signal sets and a history concentration diagnostic result corresponding to each of the history vibration signal sets; and taking the trained machine learning model as the concentration model.

For example, regarding to inhaled medications for lung disease, the inspiration system related symptom sensing system 1 can record the vibration signals of the organism continuously after the drug has taken. In the meantime, drug concentrations in blood can be recorded through drawing blood from the organism at multiple time points. Furthermore, the drug concentration trend (i.e., history concentration diagnostic result) and multiple vibration signals (i.e., history vibration signal sets) detected by multiple receivers at the same time are taken as training data to train the machine learning model, thereby obtaining the trained model (i.e., the concentration model). Therefore, the correspondence between the drug concentration trends and the vibration signals can be established, and the processor 12 can input vibration signals and generate the drug concentration trends in blood of the organism correspondingly by using the concentration model.

It is noticed that, the model types of the classification model and the concentration model are not limited in the present disclosure. Deep learning models, neural network models, or machine learning algorithms such as decision tree, K-means clustering, Naive Bayes classifier, extreme Gradient Boosting (XGBoost) can be chose. However, organisms are varied, and there are many variables affect diagnosis. Therefore, in some embodiments, the inspiration system related symptom sensing system 1 selects supervised machine learning models or unsupervised machine learning models to build the classification model and the concentration model.

In some embodiments, the inspiration system related symptom sensing system 1 can also train multiple different models and choose the model with higher precision (i.e., competing with each other) based on the training results as the classification model and the concentration model.

Figure 2:
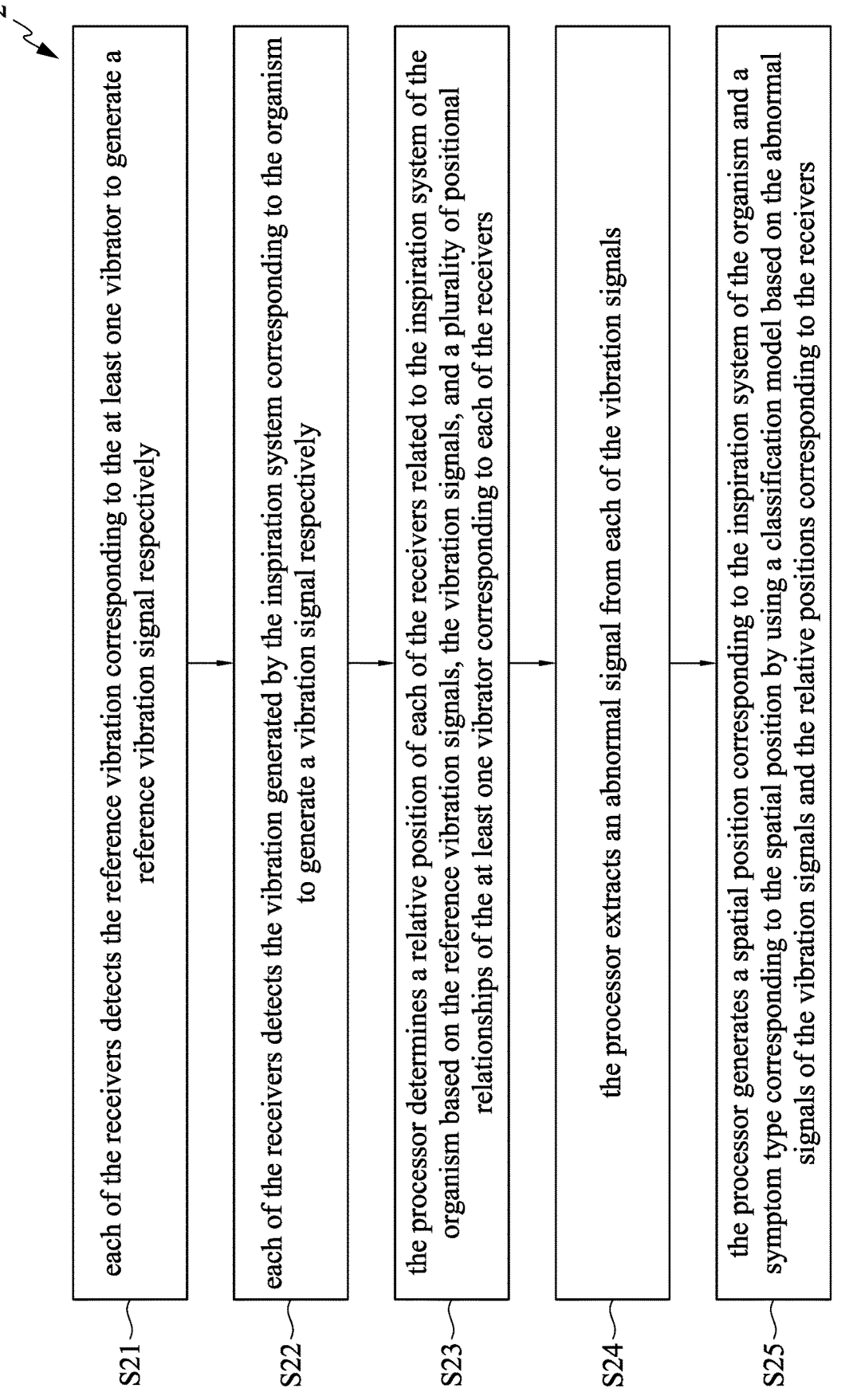
FIG. 2 is a flow diagram illustrating an inspiration system related symptom sensing method according to a second embodiment of the present disclosure.

Reference is made to FIG. 2. FIG. 2 is a flow diagram illustrating an inspiration system related symptom sensing method 2 of the second embodiment. The inspiration system related symptom sensing method 2 comprises steps S21, S22, S23, S24, and S25. The method of the embodiment shown in FIG. 2 is applicable to an inspiration system related symptom sensing system (e.g., the inspiration system related symptom sensing system 1). The inspiration system related symptom sensing system comprises a processor (e.g., the processor 12) and a patch (e.g., the patch 14), wherein the processor is communicatively connected to the patch. The patch comprises a vibrator (e.g., the vibrator V) and a plurality of receivers (e.g., the receivers R1, R2, and R3). The patch is configured to detect a vibration generated by an inspiration system of an organism, and the vibrator is configured to generate a reference vibration.

In the step S21, the receivers detect the reference vibration corresponding to the at least one vibrator to generate a reference vibration signal respectively.

In the step S22, the receivers detect the vibration generated by the inspiration system corresponding to the organism to generate a vibration signal respectively.

In the step S23, the processor determines a relative position of each of the receivers related to the inspiration system of the organism based on the reference vibration signals, the vibration signals, and a plurality of positional relationships of the at least one vibrator corresponding to each of the receivers.

In the step S24, the processor extracts an abnormal signal from each of the vibration signals.

In the step S25, the processor generates a spatial position corresponding to the inspiration system of the organism and a symptom type corresponding to the spatial position by using a classification model based on the abnormal signals of the vibration signals and the relative positions corresponding to the receivers.

In some embodiments, the inspiration system related symptom sensing method 2 further comprises the processor generating a lung sound signal corresponding to the inspiration system based on each of the vibration signals; and the processor generating the spatial position in the inspiration system of the organism and the symptom type corresponding to the spatial position based on the lung sound signals and the relative positions corresponding to the receivers.

In some embodiments, the step of the processor generating the lung sound signal further comprises the processor filtering a noise and a heart sound from the vibration signals.

In some embodiments, the step of the processor extracting the abnormal signal further comprises the processor transforming each of the vibration signals into a spectrum signal based on a frequency domain; and the processor extracting the abnormal signal based on the spectrum signals.

In some embodiments, the classification model is configured to calculate the symptom type corresponding to the vibration signals and a possibility of the organism having the symptom type.

In some embodiments, the classification model is generated through the following steps: training a machine learning model based on a plurality of history abnormal signals and a symptom diagnostic result corresponding to each of the history abnormal signals; and taking the trained machine learning model as the classification model.

In some embodiments, the inspiration system related symptom sensing method 2 further comprises the processor generating a concentration diagnostic result based on the vibration signals by using a concentration model, wherein the concentration diagnostic result is configured to represent a drug concentration trend in blood of the organism.

In some embodiments, the concentration model is generated through the following steps training a machine learning model based on a plurality of history vibration signal sets and a history concentration diagnostic result corresponding to each of the history vibration signal sets; and taking the trained machine learning model as the concentration model.

In some embodiments, the relative position of each of the receivers relative to the inspiration system of the organism and the spatial position in the inspiration system of the organism are calculated by using a Time of Flight method and a triangulation method.

In some embodiments, the inspiration system related symptom sensing method 2 further comprises the processor establishing a three-dimensional model based on the relative positions, wherein the three-dimensional model comprises a plurality of positional relationships between the patch and a plurality of organs in the inspiration system in a three-dimensional space.

Figure 3:
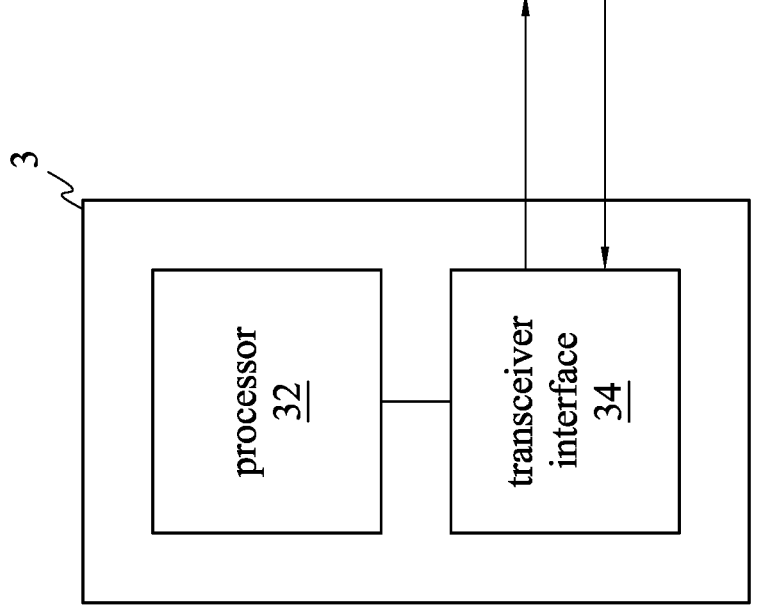
FIG. 3 is a schematic diagram illustrating an inspiration system related symptom sensing apparatus according to a third embodiment of the present disclosure.

Reference is made to FIG. 3. FIG. 3 is a schematic diagram illustrating an inspiration system related symptom sensing apparatus 3 according to a third embodiment of the present disclosure. The inspiration system related symptom sensing apparatus 3 comprises a processor 32 and a transceiver interface 34. The inspiration system related symptom sensing apparatus 3 is configured to determine the physiological state in an organism based on signals from a patch, wherein the patch can be the patch 14 of the inspiration system related symptom sensing system 1 in the first embodiment.

In some embodiments, the processor 32 can comprise a central processing unit (CPU), a multi-processor, a distributed processing system, an application specific integrated circuit (ASIC), and/or a suitable processing unit.

The transceiver interface 34 is configured to communicatively connect to the patch and transmit and receive signals with the patch, wherein the patch comprises a vibrator and a plurality of receivers. The transceiver interface 34 can comprise one or more interfaces corresponding to different communication protocols, e.g., near-field communication (NFC) interface, Bluetooth interface, ethernet network interface, Wi-Fi network interface, and/or other communication interface.

The processor 32 has the same functions as the processor 12 of the inspiration system related symptom sensing system 1 in the first embodiment and is configured to execute the same operations. For clarity, relative details will not be repeated.

First, the transceiver interface 34 receives a plurality of reference vibration signals corresponding to the at least one vibrator and a plurality of vibration signals corresponding to an inspiration system corresponding to an organism from the patch.

Next, the processor 32 determines a relative position of each of the receivers related to the inspiration system of the organism based on the reference vibration signals, the vibration signals, and a plurality of positional relationships of the at least one vibrator of the patch corresponding to each of the receivers of the patch.

Next, the processor 32 extracts an abnormal signal from each of the vibration signals.

Finally, the processor 32 generates a spatial position corresponding to the inspiration system of the organism and a symptom type corresponding to the spatial position by using a classification model based on the abnormal signals of the vibration signals and the relative positions corresponding to the receivers.

In some embodiments, the processor 32 further generates a lung sound signal corresponding to the inspiration system based on each of the vibration signals; and the processor 32 generates the spatial position in the inspiration system of the organism and the symptom type corresponding to the spatial position based on the lung sound signals and the relative positions corresponding to the receivers.

In some embodiments, the operation of the processor 32 generating the lung sound signal further comprises the processor 32 filtering a noise and a heart sound from the vibration signals.

In some embodiments, the operation of the processor 32 extracting the abnormal signal further comprises the processor 32 transforming each of the vibration signals into a spectrum signal based on a frequency domain; and the processor 32 extracting the abnormal signal based on the spectrum signals.

In some embodiments, the classification model is configured to calculate the symptom type corresponding to the vibration signals and a possibility of the organism having the symptom type.

In some embodiments, the classification model is generated through the following operations: training a machine learning model based on a plurality of history abnormal signals and a symptom diagnostic result corresponding to each of the history abnormal signals; and taking the trained machine learning model as the classification model.

In some embodiments, the processor 32 further generates a concentration diagnostic result based on the vibration signals by using a concentration model, wherein the concentration diagnostic result is configured to represent a drug concentration trend in blood of the organism.

In some embodiments, the concentration model is generated through the following operations: training a machine learning model based on a plurality of history vibration signal sets and a history concentration diagnostic result corresponding to each of the history vibration signal sets; and taking the trained machine learning model as the concentration model.

In some embodiments, the processor 32 calculates the relative position of each of the receivers relative to the inspiration system of the organism and the spatial position in the inspiration system of the organism by using a Time of Flight method and a triangulation method.

In some embodiments, the processor 32 further establishes a three-dimensional model based on the relative positions, wherein the three-dimensional model comprises a plurality of positional relationships between the patch and a plurality of organs in the inspiration system in a three-dimensional space.

Based on the embodiments mentioned above, the inspiration system related symptom sensing apparatus 3 can receive reference vibration signals and vibration signals and generate a spatial position in the inspiration system of an organism, a symptom type corresponding to the spatial position, a concentration diagnostic result and other outputs mentioned above based on the reference vibration signals and the vibration signals through operations mentioned in the first embodiment.

Therefore, physicians can provide remote medical services to patients. The patients can place the patches on their body, and the physicians receive the signals from the patches and obtain diagnostic information corresponding to the patients by using the inspiration system related symptom sensing apparatus 3. By this, the inspiration system related symptom sensing apparatus 3 can break the limitations of time and space and accomplish the operations of remote medical services.

In summary, the inspiration system related symptom sensing system, method, and apparatus provided by the present disclosure can determine the physiological state in an organism after confirming the positions of the organs in the inspiration system of the organism through detecting sounds or vibrations by receivers. The inspiration system related symptom sensing system, method, and apparatus can be applied on determining the types and positions of symptoms and estimating drug concentration trends in blood based on changes in the organism after taking drugs. Since the inspiration system related symptom sensing system, method, and apparatus perform locating through generating reference vibrations by vibrators, different organisms can be applied on and not limited by body sizes of the organisms. Therefore, not only diagnosis of human, diagnosis and experiments of other animals can also be applied on. Furthermore, remote medical services can be accomplished through operations of the patch and the inspiration system related symptom sensing apparatus.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An inspiration system related symptom sensing system, comprising:

a patch, configured to detect a vibration generated by an inspiration system corresponding to an organism, comprising:

at least one vibrator, configured to generate a reference vibration; and a plurality of receivers; and a processor, communicatively connected to the patch;

wherein the inspiration system related symptom sensing system is configured to execute the following operations:

detecting, by the receivers, the reference vibration corresponding to the at least one vibrator to generate a plurality of first vibration signals;

detecting, by the receivers, the vibration generated by the inspiration system corresponding to the organism to generate a plurality of second vibration signals;

determining, by the processor, a relative position of each of the receivers related to the inspiration system of the organism based on the first vibration signals, the second vibration signals, and a plurality of positional relationships of the at least one vibrator corresponding to the receivers;

extracting, by the processor, abnormal signals from the second vibration signals;

generating, by the processor, a spatial position corresponding to the inspiration system of the organism and a symptom type corresponding to the spatial position by using a classification model based on the abnormal signals of the second vibration signals and the relative positions corresponding to the receivers, and making a remote diagnosis to determine a physiological state in the organism based on the spatial position corresponding to the inspiration system of the organism and the symptom type corresponding to the spatial position.

2. The inspiration system related symptom sensing system of claim 1, wherein the inspiration system related symptom sensing system is further configured to:

generating, by the processor, a lung sound signal corresponding to the inspiration system based on each of the second vibration signals; and generating, by the processor, the spatial position in the inspiration system of the organism and the symptom type corresponding to the spatial position based on the lung sound signals and the relative positions corresponding to the receivers.

3. The inspiration system related symptom sensing system of claim 2, wherein the operation of the processor generating the lung sound signal further comprises:

filtering, by the processor, a noise and a heart sound from the second vibration signals.

4. The inspiration system related symptom sensing system of claim 1, wherein the operation of the processor extracting the abnormal signal further comprises:

transforming, by the processor, each of the second vibration signals into a spectrum signal based on a frequency domain; and extracting, by the processor, the abnormal signal based on the spectrum signals.

5. The inspiration system related symptom sensing system of claim 1, wherein the classification model is configured to calculate the symptom type corresponding to the second vibration signals and a possibility of the organism having the symptom type.

6. The inspiration system related symptom sensing system of claim 1, wherein the classification model is generated through the following operations:

training a machine learning model based on a plurality of history abnormal signals and a symptom diagnostic result corresponding to each of the history abnormal signals; and taking the trained machine learning model as the classification model.

7. The inspiration system related symptom sensing system of claim 1, wherein the inspiration system related symptom sensing system is further configured to:

generating, by the processor, a concentration diagnostic result based on the second vibration signals by using a concentration model.

8. The inspiration system related symptom sensing system of claim 7, wherein the concentration model is generated through the following operations:

training a machine learning model based on a plurality of history vibration signal sets and a history concentration diagnostic result corresponding to each of the history vibration signal sets; and taking the trained machine learning model as the concentration model.

9. The inspiration system related symptom sensing system of claim 1, wherein the processor calculates the relative position of each of the receivers relative to the inspiration system of the organism and the spatial position in the inspiration system of the organism by using a Time of Flight method and a triangulation method.

10. The inspiration system related symptom sensing system of claim 1, wherein the inspiration system related symptom sensing system is further configured to:

establishing, by the processor, a three-dimensional model based on the relative positions, wherein the three-dimensional model comprises a plurality of positional relationships between the patch and a plurality of organs in the inspiration system in a three-dimensional space.

11. An inspiration system related symptom sensing apparatus, comprising:

a transceiver interface, communicatively connected to a patch, wherein the patch comprises at least one vibrator and a plurality of receivers; and a processor, electrically connected to the transceiver interface;

wherein the inspiration system related symptom sensing apparatus is configured to execute the following operations:

receiving, by the transceiver interface, a plurality of first vibration signals corresponding to the at least one vibrator and a plurality of second vibration signals corresponding to an inspiration system corresponding to an organism from the patch;

determining, by the processor, a relative position of each of the receivers related to the inspiration system of the organism based on the first vibration signals, the second vibration signals, and a plurality of positional relationships of the at least one vibrator of the patch corresponding to each of the receivers of the patch;

extracting, by the processor, abnormal signals from the second vibration signals;

generating, by the processor, a spatial position corresponding to the inspiration system of the organism and a symptom type corresponding to the spatial position by using a classification model based on the abnormal signals of the second vibration signals and the relative positions corresponding to the receivers; and making a remote diagnosis to determine a physiological state in the organism based on the spatial position corresponding to the inspiration system of the organism and the symptom type corresponding to the spatial position.

12. An inspiration system related symptom sensing method, being adapted for use in an inspiration system related symptom sensing system, wherein the inspiration system related symptom sensing system comprises a processor and a patch, the patch comprises at least one vibrator and a plurality of receivers, and the inspiration system related symptom sensing method comprises:

detecting, by the receivers, a reference vibration corresponding to the at least one vibrator to generate a plurality first vibration signals;

detecting, by the receivers, the vibration generated by the inspiration system corresponding to an organism to generate a plurality of second vibration signals;

determining, by the processor, a relative position of each of the receivers related to the inspiration system of the organism based on the first vibration signals, the second vibration signals, and a plurality of positional relationships of the at least one vibrator corresponding to each of the receivers;

extracting, by the processor, abnormal signals from the second vibration signals;

generating, by the processor, a spatial position corresponding to the inspiration system of the organism and a symptom type corresponding to the spatial position by using a classification model based on the abnormal signals of the second vibration signals and the relative positions corresponding to the receivers; and making a remote diagnosis to determine a physiological state in the organism based on the spatial position corresponding to the inspiration system of the organism and the symptom type corresponding to the spatial position.

13. The inspiration system related symptom sensing method of claim 12, further comprising:

generating, by the processor, a lung sound signal corresponding to the inspiration system based on the second vibration signals; and generating, by the processor, the spatial position in the inspiration system of the organism and the symptom type corresponding to the spatial position based on the lung sound signals and the relative positions corresponding to the receivers.

14. The inspiration system related symptom sensing method of claim 13, wherein the step of the processor generating the lung sound signal further comprises:

filtering, by the processor, a noise and a heart sound from the second vibration signals.

15. The inspiration system related symptom sensing method of claim 12, wherein the step of the processor extracting the abnormal signal further comprises:

transforming, by the processor, each of the second vibration signals into a spectrum signal based on a frequency domain; and extracting, by the processor, the abnormal signal based on the spectrum signals.

16. The inspiration system related symptom sensing method of claim 12, wherein the classification model is configured to calculate the symptom type corresponding to the second vibration signals and a possibility of the organism having the symptom type.

17. The inspiration system related symptom sensing method of claim 12, wherein the classification model is generated through the following steps:

training a machine learning model based on a plurality of history abnormal signals and a symptom diagnostic result corresponding to each of the history abnormal signals; and taking the trained machine learning model as the classification model.

18. The inspiration system related symptom sensing method of claim 12, further comprising:

generating, by the processor, a concentration diagnostic result based on the second vibration signals by using a concentration model.

19. The inspiration system related symptom sensing method of claim 18, wherein the concentration model is generated through the following steps:

training a machine learning model based on a plurality of history vibration signal sets and a history concentration diagnostic result corresponding to each of the history vibration signal sets; and taking the trained machine learning model as the concentration model.

20. The inspiration system related symptom sensing method of claim 12, wherein the relative position of each of the receivers relative to the inspiration system of the organism and the spatial position in the inspiration system of the organism are calculated by using a Time of Flight method and a triangulation method.

* * * * *